US012806164B2

(12) United States Patent
Chung et al.

(10) Patent No.: US 12,806,164 B2
(45) Date of Patent: Nov. 24, 2026

(54) METHODS FOR TREATING AUTISM SPECTRUM DISORDERS (ASD)

(71) Applicant: SK BIOPHARMACEUTICALS CO., LTD., Gyeonggi-do (KR)

(72) Inventors: Jin Yong Chung, Gyeonggi-do (KR); Seok Hwan Cho, Gyeonggi-do (KR); Hyun Seok Lee, Gyeonggi-do (KR); Ho Won Kang, Gyeonggi-do (KR); Yong Do Kwak, Gyeonggi-do (KR); Min Jae Jo, Gyeonggi-do (KR)

(73) Assignee: SK BIOPHARMACEUTICALS CO., LTD., Gyeonggi-do (KR)

( * ) Notice: Subject to any disclaimer, the term of this patent is extended or adjusted under 35 U.S.C. 154(b) by 311 days.

(21) Appl. No.: 18/565,188

(22) PCT Filed: Jun. 10, 2022

(86) PCT No.: PCT/KR2022/008238

§ 371 (c)(1), (2) Date: Nov. 29, 2023

(87) PCT Pub. No.: WO2022/260484

PCT Pub. Date: Dec. 15, 2022

(65) Prior Publication Data

US 2024/0261248 A1 Aug. 8, 2024

Related U.S. Application Data

(60) Provisional application No. 63/209,463, filed on Jun. 11, 2021.

(51) Int. Cl.

*A61K 31/27* (2006.01)
*A61P 25/00* (2006.01)

(52) U.S. Cl.

CPC .............. *A61K 31/27* (2013.01); *A61P 25/00* (2018.01)

(58) Field of Classification Search

CPC ................................ A61K 31/27; A61P 25/00
See application file for complete search history.

(56) References Cited

U.S. PATENT DOCUMENTS 5,756,817 A 5/1998 Choi et al.

FOREIGN PATENT DOCUMENTS

| | | | |
|---|---|---|---|
| JP | 2020-530837 | A | 10/2020 |
| WO | WO-2010/020585 | A1 | 2/2010 |
| WO | WO-2011/055965 | A2 | 5/2011 |
| WO | WO-2016/061488 | A1 | 4/2016 |
| WO | 2019/027941 | A1 | 2/2019 |
| WO | WO-2019/098630 | A1 | 5/2019 |

OTHER PUBLICATIONS

International Search Report from corresponding PCT Application No. PCT/KR2022/008238, dated Sep. 19, 2022.

Reiersen, A. M., et al., "Commentary on 'Selective serotonin reuptake inhibitors (SSRIs) for autism spectrum disorders (ASD)'", Evid. based child health, 2011, vol. 6, pp. 1082-1085.

Mohan Gomathi et al., Journal of Autism and Developmental Disorders, 2020, vol. 50, No. 8, pp. 2740-2764.

Enza Lacivita et al., Journal of Medicinal Chemistry, 2017, vol. 60, No. 22, pp. 9114-9141.

Extended European Search Report from corresponding EP Application No. 22820611.6, dated Apr. 8, 2025.

Marotta, R., et al., "The Neurochemistry of Autism", Brain Sciences, 2020, vol. 10, No. 163, pp. 1-18.

*Primary Examiner* — Timothy R Rozof

(74) *Attorney, Agent, or Firm* — Harness, Dickey & Pierce, P.L.C.

(57) ABSTRACT

The present disclosure relates generally to methods of treating autism spectrum disorders (ASD), using a compound of Formula (I).

20 Claims, 3 Drawing Sheets

[Fig. 1]
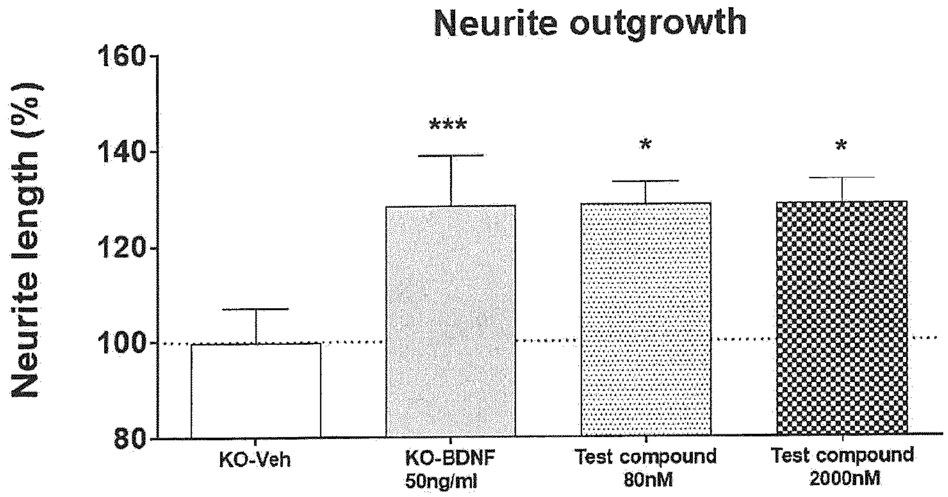
[Fig. 2A]
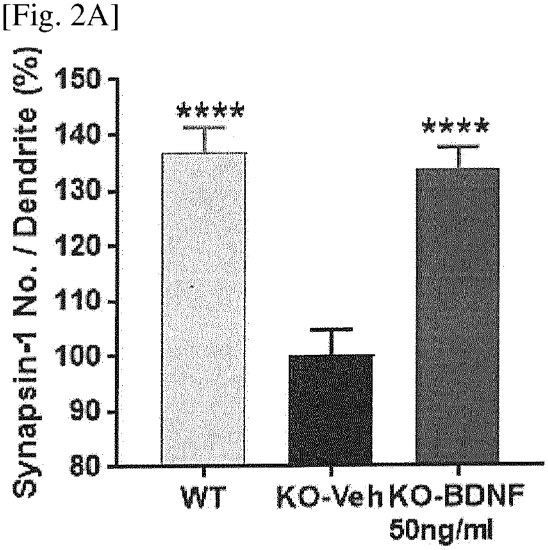
[Fig. 2B]
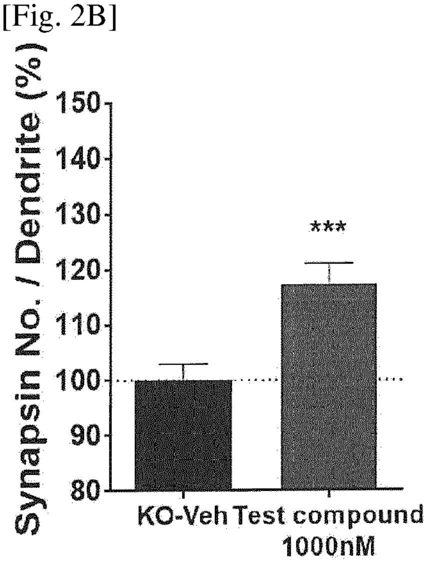

[Fig. 3A]
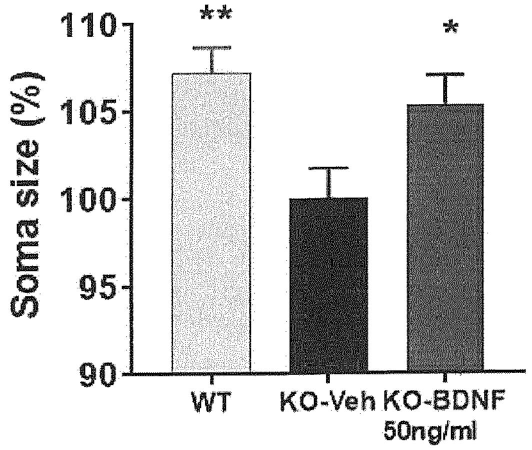
[Fig. 3B]
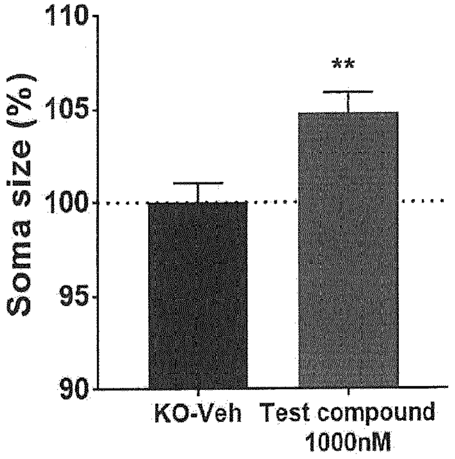
[Fig. 4]
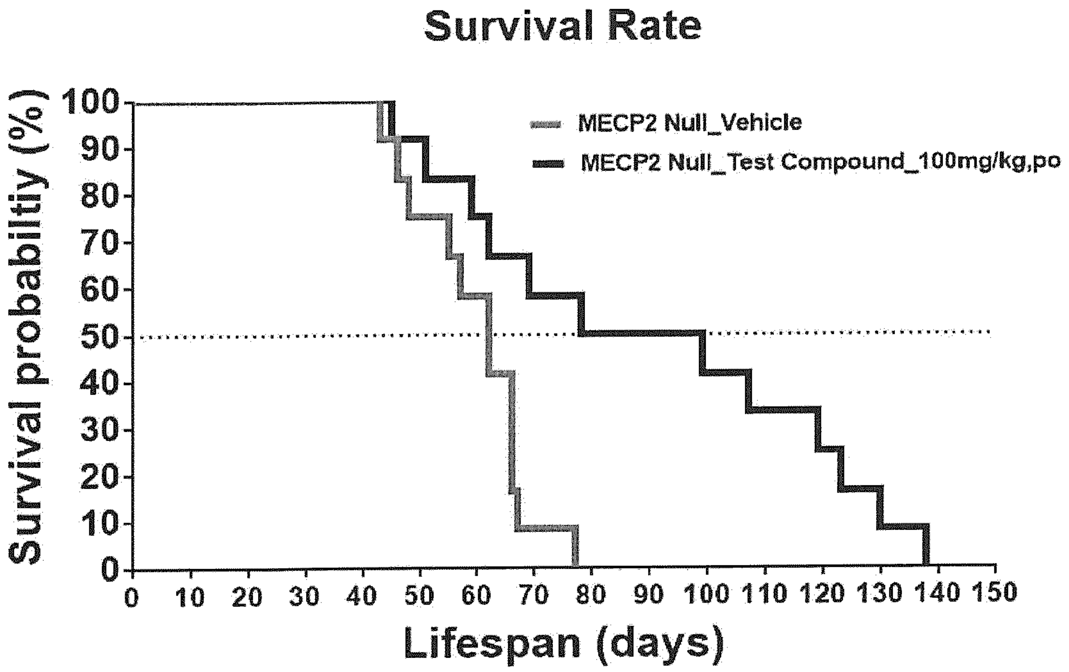

[Fig. 5]
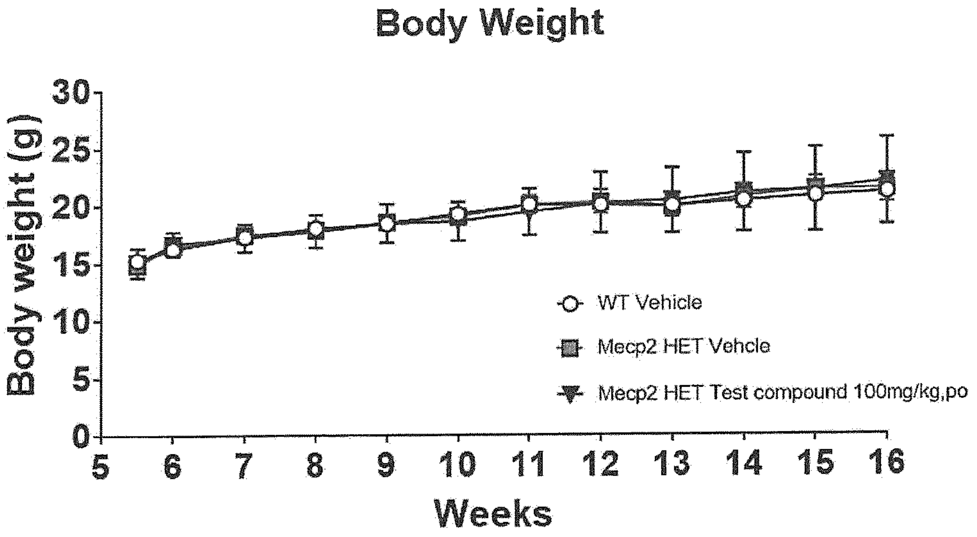
[Fig. 6]
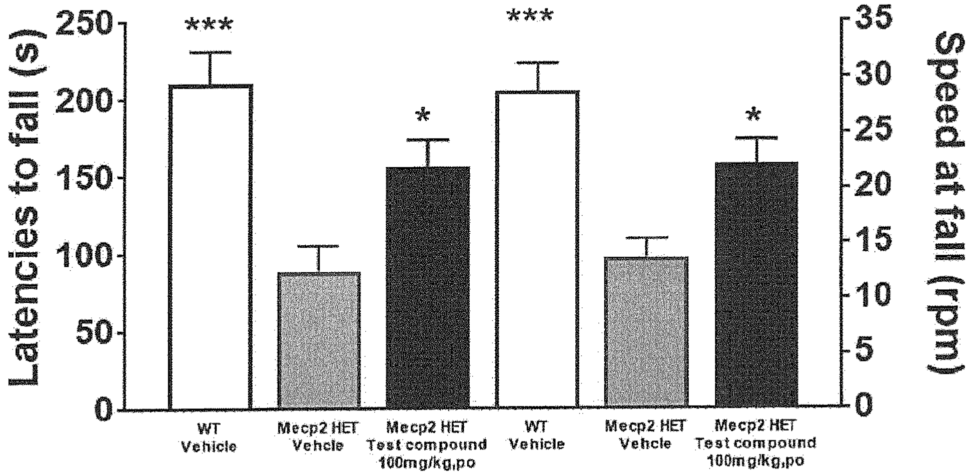
[Fig. 7]
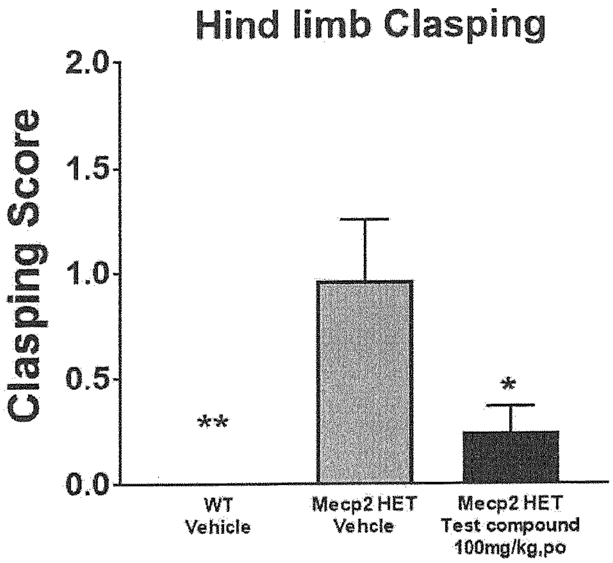

METHODS FOR TREATING AUTISM SPECTRUM DISORDERS (ASD)

CROSS-REFERENCE TO RELATED APPLICATIONS

This application is a national phase application of PCT Application No. PCT/KR2022/008238, filed on Jun. 10, 2022, which claims priority to U.S. Patent Application No. 63/209,463, filed on Jun. 11, 2021. The entire disclosures of the applications identified in this paragraph are incorporated herein by references.

TECHNICAL FIELD

The present disclosure relates generally to the fields of pharmacology and neurology such as methods of treating neurodevelopmental disorders. More specifically, this disclosure provides methods of using carbamate compounds for the treatment of neurodevelopmental disorders such as autism spectrum disorders (ASD) including autism, autistic disorder, Asperger Syndrome, Rett syndrome, Angelman syndrome, Williams syndrome, pervasive developmental disorder not otherwise specified (PDD-NOS), childhood disintegrative disorder, and/or Smith-Magenis syndrome.

BACKGROUND ART

Autism spectrum disorder (ASD) is a complex neurodevelopmental condition that involves learning disabilities, intellectual disability (also known as mental retardation), conduct disorders, cerebral palsy, and impairments in vision, hearing, movement, speech and language. Autism spectrum disorders include autism, autistic disorder, Asperger syndrome, Rett syndrome, Angelman syndrome, Williams syndrome, Pervasive Developmental Disorder Not Otherwise Specified (PDD-NOS), Childhood Disintegrative Disorder, and Smith-Magenis Syndrome.

The clinical course of the disease consists of an initial normal development until 6 to 18 months of age followed by an arrest of brain development, severely impaired expressive language, the development of stereotypic hand movements, and the appearance of gait ataxia and truncal apraxia/ataxia between 1 and 4 years of age. The affected individuals are primarily young females, and more than 95% of patients carry de novo mutation(s) in the Methyl-CpG-Binding Protein 2 (MeCP2) gene. MeCP2 expression in the brain is tightly regulated, and its altered expression leads to abnormal brain function, implicating MeCP2 in some cases of autism spectrum disorders in RTT pathobiology and disease mechanism. (Biomolecules 2021, 11, 75)

Other frequent symptoms include breathing dysfunction, electroencephalography (EEG) abnormalities, seizures, spasticity, scoliosis, and reduced growth. (Biomolecules 2021, 11, 75)

Rett-like syndromes share a range of clinical characteristics, including intellectual disability (ID) with or without regression, epilepsy, infantile encephalopathy, postnatal microcephaly, features of autism spectrum disorder, and variable other neurological symptoms. (Mol Syndromol. 2012 April; 2(3-5): 217-234.)

There is no cure for ASDs including Rett syndrome and there's currently no medication to treat it. It has been merely reported that some medicines can be used for related symptoms such as seizures, sleep problem including breath problem, anxiety, depression and trouble focusing.

DISCLOSURE OF INVENTION

Solution to Problem

The present disclosure provides a method of treating or preventing autism spectrum disorders (ASD) or one or more symptoms of ASD in a subject comprising, administering to a subject in need of such treatment a therapeutically effective amount of a compound of Formula (I):

(I)

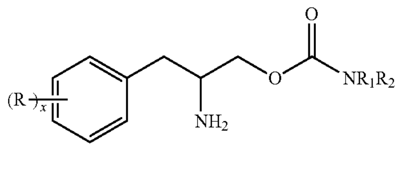

or a pharmaceutically acceptable salt or ester thereof;

wherein R is selected from the group consisting of —H, alkyl, halo, alkoxy, nitro, hydroxy, haloalkyl, and thioalkoxy;

x is an integer of 1 to 3, with the proviso that R may be the same or different when x is 2 or 3; and $R_1$ and $R_2$ are independently selected from the group consisting of —H, alkyl, aryl, arylalkyl, and cycloalkyl; or $R_1$ and $R_2$ together form a 5 to 7-membered heterocyclic group which is optionally substituted with alkyl or aryl, wherein the heterocyclic group can comprise 1 to 2 nitrogen atoms and 0 to 1 oxygen atom, wherein the nitrogen atoms are not directly connected with each other or with the oxygen atom.

In an embodiment, R is selected from the group consisting of —H, lower alkyl of 1 to 8 carbon atoms, halo selected from F, Cl, Br and I, alkoxy containing 1 to 3 carbon atoms, nitro, hydroxy, trifluoromethyl, and thioalkoxy containing 1 to 3 carbon atoms;

x is an integer of 1 to 3, with the proviso that R may be the same or different when x is 2 or 3; and $R_1$ and $R_2$ can be the same or different from each other and are independently selected from the group consisting of —H, lower alkyl of 1 to 8 carbon atoms, aryl, arylalkyl, and cycloalkyl of 3 to 7 carbon atoms; $R_1$ and $R_2$ can be joined to form a 5 to 7-membered heterocyclic group substituted with a member selected from the group consisting of —H, alkyl, and aryl, wherein the heterocyclic group can comprise 1 to 2 nitrogen atoms and 0 to 1 oxygen atom, wherein the nitrogen atoms are not directly connected with each other or with the oxygen atom.

The present disclosure also provides a use, for the preparation of a medicament for the treatment or prevention of autism spectrum disorders (ASD) or one or more symptoms of ASD, of a compound of Formula (I):

(I)

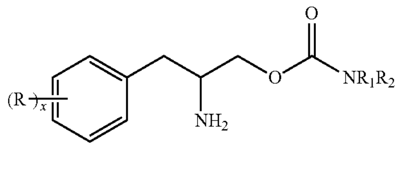

or a pharmaceutically acceptable salt or ester thereof;

wherein R, $R_1$, $R_2$, and x are as defined above.

The present disclosure also provides a pharmaceutical composition, for use in the treatment or prevention of autism spectrum disorders (ASD) or one or more symptoms of ASD, comprising a compound of the Formula (I):

(I)

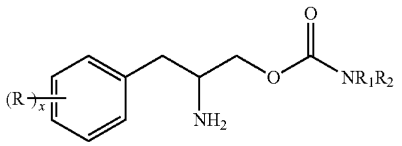

or a pharmaceutically acceptable salt or ester thereof; wherein R, $R_1$, $R_2$, and x are as defined above.

In some embodiments, the compound of Formula (I) is a compound of Formula (Ia):

(Ia)

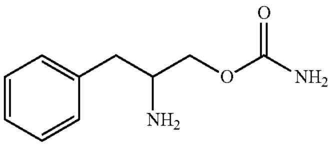

or a pharmaceutically acceptable salt or ester thereof.

In some embodiments, the compound of Formula (I) is a compound of Formula (Ib):

(Ib)

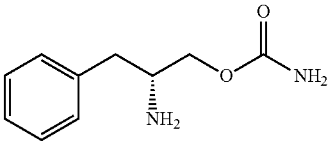

or a pharmaceutically acceptable salt or ester thereof. This compound is named (R)-(beta-amino-benzenepropyl) carbamate or O-carbamoyl-(D)-phenylalaninol and has alternatively been called ADX-N05, SKL-N05, YKP10A, and R228060.

In some embodiments, the autism spectrum disorders (ASD) is selected from the group consisting of autism, autistic disorder, Asperger syndrome, Rett syndrome, Angelman syndrome, Williams syndrome, Pervasive Developmental Disorder Not Otherwise Specified (PDD-NOS), Childhood Disintegrative Disorder, and Smith-Magenis Syndrome.

BRIEF DESCRIPTION OF DRAWINGS

FIGS. 1, 2, and 3 show the effect of administering the Test compound on the morphological recovery of MeCP2 KO primary neuron, in view of neurite outgrowth, synaptogenesis, and soma size, respectively.

FIG. 4 shows the effects of Test compound on increased survival duration in MeCP2 KO mice (Null) compared to saline-treated MeCP2 KO mice (Null).

FIG. 5 shows the effect of administering the Test compound on the body weight change in MeCP2 KO mice (HET) compared to saline-treated MeCP2 KO mice (HET) and WT mice.

FIGS. 6 and 7 show the effect of administering the Test compound on motor function in MeCP2 KO mice (HET), compared to saline-treated MeCP2 KO mice (HET) and saline-treated WT mice in view of accelerating rotarod and hindlimb clasping test, respectively.

MODE FOR THE INVENTION

The invention described in this disclosure is based in part on the discovery that the compound of Formula (I) has novel and unique pharmacological properties. Specifically, the compound of Formula (I) has shown in both in-vitro and animal models to have effects on treating, preventing, or ameliorating ASD such as Rett syndrome. The compound of Formula (I) ameliorates structural and behavioral abnormalities with loss-of-function mutations of the gene encoding Methyl-CpG binding protein 2 (MeCP2) in MeCP2 knock out primary neurons and animals. MeCP2 gene mutations are the cause of most cases of Rett syndrome, which shares key features with other autism spectrum disorders. Further, the recently published papers reported the mutation of MeCP2-P152L, MeCP2-R294X, or MeCP2-P376S is identified in autism patients, which affects proper physiological functions of the MeCP2 protein, and thus it may contribute to the pathogenesis of autism (Molecular Autism volume 8, Article number: 43 (2017)).

Therefore, the compounds of Formula 1 are suitable for use in treatment or prevention for autism spectrum disorders (ASD) or one or more symptoms of ASD. In some embodiments, the present disclosure provides a method of preventing or reducing the severity of autism spectrum disorders (ASD). The method comprises administering to a subject in need thereof a therapeutically effective amount of a compound selected from the group consisting of phenylalkylamino carbamates of Formula (I):

(I)

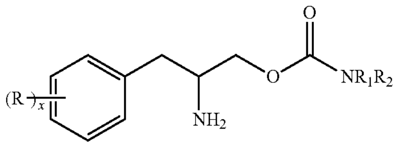

or an enantiomer, diastereomer, racemate or mixtures thereof, or a pharmaceutically acceptable salt or ester thereof;

wherein R is selected from the group consisting of —H, alkyl, halo, alkoxy, nitro, hydroxy, haloalkyl, and thioalkoxy;

x is an integer of 1 to 3, with the proviso that R may be the same or different when x is 2 or 3; and $R_1$ and $R_2$ are independently selected from the group consisting of —H, alkyl, aryl, arylalkyl, and cycloalkyl; or $R_1$ and $R_2$ together form a 5 to 7-membered heterocyclic group which is optionally substituted with alkyl or aryl, wherein the heterocyclic group can comprise 1 to 2 nitrogen atoms and 0 to 1 oxygen atom, wherein the nitrogen atoms are not directly connected with each other or with the oxygen atom.

The method also includes the use of a compound of Formula (I) wherein R, $R_1$ and $R_2$ are selected from —H, having the structure of Formula (Ia):

(Ia)

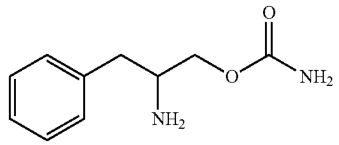

The method also includes the use of the D enantiomer compound of Formula (l) or an enantiomeric mixture wherein the D enantiomer selected from the group consisting of Formula (la) predominates wherein R, $R_1$ and $R_2$ are selected from —H, i.e., the compound is O-carbamoyl-(D)-phenylalaninol, having the structure of Formula (lb); (i.e., in the D enantiomer, as shown, the amine group on the chiral carbon is orientated into the plane of the paper.)

(Ib)

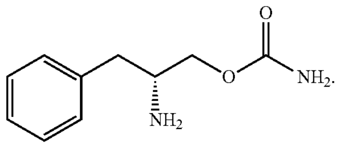

For enantiomeric mixtures wherein one enantiomer selected from the group consisting of Formula (l) predominates, in particular embodiments, an enantiomer selected from the group consisting of Formula (l) predominates to the extent of about 90% or greater. In some other embodiments, an enantiomer of Formula (l) predominates to the extent of about 98% or greater.

In an embodiment, a compound of Formula (l) consists of the (D) enantiomer of the structure shown below, wherein R, $R_1$, $R_2$ are all —H, and wherein in the structure shown below the amine group is directed down from the plane of the paper,

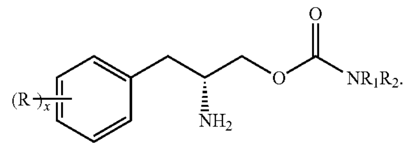

This compound is the (R) enantiomer and the chemical name is (R)-(beta-amino-benzenepropyl) carbamate. This compound is the dextro-rotary enantiomer and can therefore also be named O-carbamoyl-(D)-phenylalaninol and is referred to herein as the "Test compound". The two chemical names may be used interchangeably in this specification.

This compound has been tested in a number of animal models and has demonstrated effects including strongly ameliorated structural and behavioral abnormalities with loss-of-function mutations of the gene encoding Methyl-CpG binding protein 2 (MeCP2).

The compounds of Formula (l) can be synthesized by methods known in the art. The salts and esters of the compounds of Formula (l) can be prepared by treating the compound with a suitable mineral or organic acid (HX) in suitable solvent or by other means well known in the art.

Details of the above reactions schemes for synthesizing compounds of Formula (l) as well as representative examples on the preparation of specific compounds have been described in U.S. Pat. Nos. 5,705,640, 5,756,817, 5,955,499, and 6,140,532, all incorporated herein by reference in their entirety.

Some of the compounds of the disclosure have at least one and possibly more asymmetric carbon atoms. The present invention includes within its scope the stereochemically pure isomeric forms of the compounds as well as their racemates. Stereochemically pure isomeric forms can be obtained by the application of art known principles. Diastereoisomers may be separated by physical separation methods such as fractional crystallization and chromatographic techniques, and enantiomers may be separated from each other by the selective crystallization of the diastereomeric salts with optically active acids or bases or by chiral chromatography. Pure stereoisomers may also be prepared synthetically from appropriate stereochemically pure starting materials, or by using stereoselective reactions.

During any of the processes for preparation of the compounds of the present disclosure, it may be necessary and/or desirable to protect sensitive or reactive groups on any of the molecules concerned. This may be achieved by means of conventional protecting groups, such as those described in Protective Groups in Organic Chemistry, ed. J. F. W. McOmie, Plenum Press, 1973; and T. W. Greene & P. G. M. Wuts, Protective Groups in Organic Synthesis, Third Edition, John Wiley & Sons, 1999. The protecting groups may be removed at a convenient subsequent stage using methods known from the art.

Other embodiments include the use, for the preparation of a medicament for the treatment or prevention of autism spectrum disorders (ASD), of one of the compounds or enantiomers or enantiomeric mixtures described above or a pharmaceutically acceptable salt or ester thereof.

Definitions

For convenience, certain terms employed in the specification, examples, and appended claims are collected here. This invention is not limited to the particular methodology, protocols, animal species or genera, and reagents described, as such may vary.

The term "therapeutically effective amount" as used herein, means that amount of active compound or pharmaceutical agent that elicits the biological or medicinal response in a tissue system, animal or human that is being sought by a researcher, veterinarian, medical doctor or other clinician, which includes alleviation of one or more of the signs or symptoms of the disease or disorder being treated. And it is to be understood that a therapeutically effective amount of an agent or combinatory therapy may vary according to factors such as the disease state, age, and weight of the subject, and the ability of the agent to elicit a desired response in the subject. Dosage regimens may be adjusted to provide the optimum therapeutic response. A therapeutically effective amount is also one in which any toxic or detrimental effects of the active compound are outweighed by the therapeutically beneficial effects.

The term "prophylactically effective amount" is intended to mean that amount of a pharmaceutical drug that will prevent or reduce the risk of occurrence of the biological or medical event that is sought to be prevented, in a tissue, a system, animal or human, by a researcher, veterinarian, medical doctor or other clinician.

The term "pharmaceutically acceptable salts or esters" means non-toxic salts or esters of the compounds employed in this disclosure which are generally prepared by reacting the free acid with a suitable organic or inorganic base or the free base with a suitable organic or inorganic acid. Examples of such salts include, but are not limited to, acetate, benzenesulfonate, benzoate, bicarbonate, bisulfate, bitartrate, borate, bromide, calcium, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynapthoate, iodide, isothionate, lactate, lactobionate, laurate, malate, maleate, mandelate, mesylate, methylbromide, methylnitrate, methylsulfate, mucate, napsylate, nitrate, oleate, oxalate, pamaote, palmitate, panthothenate, phosphate/diphosphate, polygalacturonate, potassium, salicylate, sodium, stearate, subacetate, succinate, tannate, tartrate, teoclate, tosylate, triethiodide, and valerate.

The terms "subject" or "patient" are used herein interchangeably and as used herein mean any mammal, including but not limited to human beings including a human patient or subject, to which the compositions of the disclosure can be administered. The term mammals include human patients and non-human primates, as well as experimental animals such as rabbits, rats, and mice, and other animals. The subject or patient may be diagnosed by observing deceleration of growth or regression in language, or reduced motor skills including purposeful hand movements. The subject may also have one or more symptoms or disorders selected from the group consisting of stereotypical movements, autistic features, panic-like attacks, sleep cycle disturbances, tremors, seizures, respiratory dysfunctions (episodic apnea, hyperpnea), apraxia, dystonia, dyskinesia, hypotonia, progressive kyphosis or scoliosis and severe cognitive impairment.

The term "treating" or "treatment" as used herein, refers to any indicia of success in the prevention or amelioration of an injury, pathology or condition, including any objective or subjective parameter such as abatement; remission; diminishing of symptoms or making the injury, pathology, or condition more tolerable to the patient; slowing in the rate of degeneration or decline or worsening of the illness; making the final point of worsening less debilitating; or improving a subject's physical or mental well-being. The treatment or amelioration of symptoms can be based on objective or subjective parameters; including the results of improvement of apraxia, dystonia, dyskinesia, hypotonia, scoliosis, motor skill including repetitive hand movement and stereotypical movement, and Enhancing of language and swallowing ability, cognitive and respiratory functions.

The term "preventing" or "prevention" as used herein, consists of preventing the onset of an injury, pathology or condition, that is, preventing the disease or pathological condition from occurring in a subject (preferably a mammal and, more preferably, a human), particularly when said subject is predisposed to develop the pathological condition.

The term "therapeutic effect" as used herein, refers to the effective provision of the above-described action.

The term "concomitant administration" or "combination administration" of a compound, therapeutic agent or known drug with a compound of the present disclosure means administration of a known medication or drug and, in addition, the one or more compounds of the disclosure at such time that both the known drug and the compound will have a therapeutic effect. In some embodiments, this therapeutic effect will be synergistic. Such concomitant administration can involve concurrent (i.e., at the same time), prior, or subsequent administration of the known drug with respect to the administration of a compound of the present disclosure. A person of ordinary skill in the art, would have no difficulty determining the appropriate timing, sequence and dosages of administration for particular drugs and compounds of the present disclosure.

In some embodiments, the compounds of this disclosure will be used, either alone or in combination with each other or in combination with one or more other therapeutic medications as described above, or their salts or esters, for manufacturing a medicament for the purpose of providing treatment for ASD to a patient or subject in need thereof.

The term "alkyl" refers to a straight or branched chain hydrocarbonyl group. In an embodiment, alkyl has from 1 to 12 carbon atoms. In some embodiments, alkyl is a "$C_1$-$C_4$ alkyl" which refers to aliphatic hydrocarbons having from 1 to 4 carbon atoms. Examples of alkyl groups include, but are not limited to, methyl, ethyl, propyl, isopropyl, butyl, isobutyl, t-butyl, pentyl, hexyl, heptyl, octyl, nonyl and decyl.

The term "Test compound" or "TEST COMPOUND" means the hydrochloride salt of (R)-(beta-amino-benzenepropyl) carbamate which can also be named Ocarbamoyl-(D)-phenylalaninol. This compound is the (R) enantiomer, shown as Formula (Ib), structurally and is also the dextrorotary enantiomer.

Autism spectrum disorders (ASD) are a collection of linked developmental disorders, characterized by abnormalities in social interaction and communication, restricted interests and repetitive behaviors. The autism spectrum disorders (ASD) includes, but is not limited to, autism, autistic disorder, Asperger syndrome, Rett syndrome, Angelman syndrome, Williams syndrome, Pervasive Developmental Disorder Not Otherwise Specified (PDD-NOS), Childhood Disintegrative Disorder, and Smith-Magenis Syndrome.

Autism is a highly variable neurodevelopmental disorder. It is typically diagnosed during infancy or early childhood, with overt symptoms often apparent from the age of 6 months, and becoming established by 2-3 years. According to the criteria set out in the DSM-IV, diagnosis of autism requires a triad of symptoms to be present, including (a) impairments in social interaction, (b) impairments in communication and (c) restricted and repetitive interests and behaviors. Other dysfunctions, such as atypical eating, are also common but are not essential for diagnosis. Of these impairments, social interaction impairments are particularly important for diagnosis, and two of the following impairments must be present for a diagnosis of autism:

(i) impairments in the use of multiple nonverbal behaviors (e.g. eye contact) to regulate social interaction;
(ii) failure to develop peer relationships appropriate to developmental level;
(iii) lack of spontaneous seeking to share enjoyment, interests, or achievements;
(iv) lack of social or emotional reciprocity.

Importantly, autism shares features of Rett Syndrome in relation to neuronal connectivity. All three disorders are characterized by defects in synaptic function and neuronal connectivity. This is reflected in studies of post mortem human brain in these patient groups, which all show failure to form normal synaptic connections. This is reflected in altered morphological characteristics, being either a reduction in neuron dendritic spine density, or enhanced dendritic spine density but associated with immature synapses. This is reflected in animal models of autism, Rett Syndrome and Fragile X Syndrome, which are based on genetic changes known to be pathological in these disorders. In these animal models, neuronal connectivity defects are revealed morphologically, and also as a failure of Long Term Potentiation (LTP).

Autistic Disorder is referred to several different ways including early infantile autism, childhood autism, or Kanner's autism.

Asperger syndrome or Asperger Disorder is similar to autism, and shares certain features. Like autism, Asperger syndrome is also characterized by impairment in social interaction and this is accompanied by restricted and repetitive interests and behavior. Thus, diagnosis of Asperger syndrome is characterized by the same triad of impairments as autism. However, it differs from the other ASDs by having no general delay in language or cognitive development and no deficit in interest in the subject's environment. Moreover, Asperger syndrome is typically less severe in symptomology than classical autism and Asperger's patients may function with self-sufficiency and lead relatively normal lives.

Rett Syndrome (RTT) is a neurodevelopmental disorder that almost exclusively affects females (1 in 10:000 live births). RTT is classified as an autism spectrum disorder (Diagnostic and Statistical Manual of Mental Disorders, Fourth Edition-Revised (DSM-IV-R). Approximately 16,000 patients are currently affected by it in the U.S.A. (Rett Syndrome Research Trust data). For a diagnosis of Rett syndrome, the following symptoms are characteristic: impaired development from age 6-18 months; slowing of the rate of head growth starting from between age 3 months and 4 years; severely impaired language; repetitive and stereotypic hand movements; and gait abnormalities, e.g. toe-walking or unsteady stiff-legged walk. There are in addition, a number of supportive criteria that may help diagnosis of Rett Syndrome, but are not essential for a diagnosis. These include breathing difficulties, EEG abnormalities, seizures, muscle rigidity and spasticity, scoliosis (curving of the spine), teeth-grinding, small hands and feet in relation to height, growth retardation, decreased body fat and muscle mass, abnormal sleep patterns, irritability or agitation, chewing and/or swallowing difficulties, poor circulation and constipation.

The onset of RTT usually begins between 6-18 months of age with a slowing of development and growth rates. This is followed by a regression phase (typically in children aged 1-4 years of age), pseudo-stationary phase (2-10 years of age) and a subsequent progressive late motor deterioration state. RTT symptoms include sudden deceleration of growth and regression in language and motor skills including purposeful hand movements being replaced by stereotypical movements, autistic features, panic-like attacks, sleep cycle disturbances, tremors, seizures, respiratory dysfunctions (episodic apnea, hyperpnea), apraxia, dystonia, dyskinesia, hypotonia, progressive kyphosis or scoliosis and severe cognitive impairment. Most RTT patients survive into adulthood with severe disabilities and require 24-hour-a-day care.

Between 85% and 95% cases of RTT are reported to be caused by a mutation of the MeCP2 gene (Amir et al. 1999. Nat Genet 23: 185-188; Rett Syndrome Research Trust)—a gene encoding methyl-CpG-binding protein 2 (MeCP2). Mecpl maps to the X-chromosome (location Xq28) and for this reason, mutations to the gene in males are usually lethal. While RTT is a genetic disorder, less than 1% of recorded cases are inherited; almost all mutations of Mecp2 occur de novo, with two thirds caused by mutations at 8 CpG dinucleotides (R106, R133, T158, R168, R255, R270, R294 and R306) located on the third and fourth exons. MeCP2+/− model may be useful for preclinical development targeting specific cortical processing abnormalities in RTT with potential relevance to ASD. (Neurobiol Dis. 2012 April; 46(1):88-92.)

MeCP2 is a protein that binds methylated CpG dinucleotides to exert transcriptional silencing of DNA in the CNS. The key effect of a reduction or absence of MeCP2 appears to be an impairment of dendritic spine development and the formation of synapses. MeCP2 expression appears to temporally correlate with brain maturation, explaining why symptoms typically appear around 18 months of age.

Angelman syndrome is a complex genetic disorder that primarily affects the nervous system. Characteristic features of this condition include delayed development, intellectual disability, severe speech impairment, and problems with movement and balance (ataxia). Rett syndrome and Angelman syndrome are neurodevelopmental disorders characterized by severe intellectual disability, microcephaly, speech disturbance, movement disorders with gait and/or truncal ataxia, and occasionally a similar facial appearance.

Williams syndrome, also known as Williams-Beuren syndrome, is a rare genetic disorder characterized by growth delays before and after birth (prenatal and postnatal growth retardation), short stature, a varying degree of mental deficiency, and distinctive facial features that typically become more pronounced with age.

Pervasive Developmental Disorder—Not Otherwise Specified (PDD-NOS) is an ASD that describes patients exhibiting some, but not all, of the symptoms associated with other well defined ASDs. The key criteria for diagnosis of an ASD include difficulty socializing with others, repetitive behaviors, and heightened sensitivities to certain stimuli. These are all found in the ASDs described above. However, autism, Asperger syndrome, Rett syndrome and childhood disintegrative disorder all have other features that enable their specific diagnosis. When specific diagnosis of one of these four disorders cannot be made, but ASD is apparent, a diagnosis of PDD-NOS is made. Such a diagnosis may result from symptoms starting at a later age than is applicable for other conditions in the spectrum.

Childhood disintegrative disorder (CDD), also known as Heller syndrome, is a condition in which children develop normally until age 2-4 years (i.e. later than in Autism and Rett syndrome), but then demonstrate a severe loss of social, communication and other skills. Childhood disintegrative disorder is very much like autism and both involve normal development followed by significant loss of language, social play and motor skills. However, childhood disintegrative disorder typically occurs later than autism, involves a more dramatic loss of skills and is far less common.

Smith-Magenis syndrome (SMS) is a developmental disorder that affects many parts of the body. The major features of this condition include mild to moderate intellectual disability, delayed speech and language skills, distinctive facial features, sleep disturbances, and behavioral problems.

In some embodiments, symptom of ASD is anxiety, impairment in social interaction, impairment in the use of multiple nonverbal behaviors, failure to develop peer relationships appropriate to developmental level, lack of spontaneous seeking to share enjoyment, interests, or achievements, lack of social or emotional reciprocity, impairment in communication, restricted and repetitive interests and behaviors, lack of spontaneous make-believe play, abnormal fear conditioning, abnormal social behavior, repetitive behavior, abnormal nocturnal behavior, seizure activity, abnormal locomotion, abnormal expression of Phospho-ERK1/2, abnormal expression of Phospho-Akt, and bradycardia.

Methods are known in the art for determining therapeutically and prophylactically effective doses for the instant pharmaceutical composition. For example, for use as a treatment for ASD, the compounds of this disclosure can be employed at a daily dose in the range of about 0.1 mg to 1000 mg usually on a regimen of 1 to 3 times per day, for an average adult human. The effective amount, however, may be varied depending upon the particular compound used, the mode of administration, the strength of the preparation, the mode of administration, and the advancement of the disease condition. In addition, factors associated with the particular patient being treated, including patient age, weight, diet and time of administration, will result in the need to adjust dosages. Typically, doses of a compound of Formula (l) would start at 10-25 mg/day or 37.5-75 mg/day and increase in increments of about 10-25 mg/day per week until side effects intervene or at intervals of at least several days or an adequate response is obtained, with a maximum dose in the range of 150 mg/day to 500 mg/day or 500 mg/day to 2000 mg/day.

The compound may be administered to a subject by any conventional route of administration, including, but not limited to, intravenous, oral, subcutaneous, intramuscular, intradermal and parenteral. Depending on the route of administration, compounds of Formula (I) can be constituted into any form. For example, forms suitable for oral administration include solid forms, such as pills, gelcaps, tablets, caplets, capsules (each including immediate release, timed release and sustained release formulations), granules, and powders. Forms suitable for oral administration also include liquid forms, such as solutions, syrups, elixirs, emulsions, and suspensions. In addition, forms useful for parenteral administration include sterile solutions, emulsions and suspensions.

To prepare the pharmaceutical compositions of this disclosure, one or more compounds of Formula (I) or salt thereof as an active ingredient is admixed with a pharmaceutical carrier according to conventional pharmaceutical compounding techniques. Carriers are necessary and inert pharmaceutical excipients, including, but not limited to, binders, suspending agents, lubricants, flavorings, sweeteners, preservatives, dyes, and coatings. In preparing compositions in oral dosage form, any of the usual pharmaceutical carriers may be employed. For example, for liquid oral preparations, suitable carriers and additives include water, glycols, oils, alcohols, flavoring agents, preservatives, coloring agents and the like; for solid oral preparations, suitable carriers and additives include starches, sugars, diluents, granulating agents, lubricants, binders, disintegrating agents and the like.

For parenteral use, the carrier will usually comprise sterile water or saline solution, though other ingredients, for example, for purposes such as aiding solubility or for preservation, may be included. Injectable suspensions may also be prepared, in which case appropriate liquid carriers, suspending agents and the like may be employed.

Because of their ease in administration, tablets and capsules represent the most advantageous oral dosage unit form, in which case solid pharmaceutical carriers are obviously employed. If desired, tablets may be sugar coated or enteric coated by standard techniques. Suppositories may be prepared, in which case cocoa butter could be used as the carrier. The tablets or pills can be coated or otherwise compounded to provide a dosage form affording the advantage of prolonged action. For example, the tablet or pills can comprise an inner dosage and an outer dosage component, the latter being in the form of an envelope over the former.

The two components can be separated by an enteric layer, which serves to resist disintegration in the stomach and permits the inner component to pass intact into the duodenum or to be delayed in release. A variety of material can be used for such enteric layers or coatings, such materials including a number of polymeric acids with such materials as shellac, cetyl alcohol and cellulose acetate.

An active ingredient may also be delivered by the use of monoclonal antibodies as individual carriers to which the compound molecules are coupled. An active ingredient may also be coupled with soluble polymers as targetable drug carriers. Such polymers can include polyvinyl-pyrrolidone, pyran copolymer, polyhydroxypropyl-methacrylamide-phenol, polyhydroxy-ethyl-aspartamide-phenol, or polyethyleneoxide-polylysine substituted with palmitoyl residues. Furthermore, an active ingredient may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacrylates and cross linked or amphipathic block copolymers of hydrogels.

In some embodiments, these compositions are in unit dosage forms such as tablets, pills, capsules, powders, granules, sterile parenteral solutions or suspensions, metered aerosol or liquid sprays, drops, ampoules, auto-injector devices or suppositories, for oral parenteral, intranasal, sublingual or rectal administration, or for administration by inhalation or insufflation.

Alternatively, the composition may be presented in a form suitable for once-weekly or once-monthly administration; for example, an insoluble salt of the active compound, such as the decanoate salt, may be adapted to provide a depot preparation for intramuscular injection.

The pharmaceutical compositions herein will contain, per dosage unit, e.g., tablet, capsule, powder, injection, teaspoonful, suppository and the like, an amount of the active ingredient necessary to deliver an effective dose as described above. For example, the pharmaceutical compositions herein can contain, per unit dosage unit, from about 10 to about 1000 mg or about 10 to about 500 mg of the active ingredient. In some embodiments, the pharmaceutical compositions contain about 1 mg to about 1000 mg of the active ingredient or any range or value therein, e.g., about 10 mg to about 500 mg, e.g., about 37.5 mg, about 75 mg, about 150 mg, or about 300 mg. In some embodiments, the range is from about 10 mg to about 300 mg or about 25 to about 200 mg of the active ingredient.

In some embodiments, a carbamate compound suitable for use in the practice of this invention is administered either singly or concomitantly with at least one or more other compounds or therapeutic agents, e.g., with other agents that may increase arousal or alertness. In these embodiments, the present disclosure provides methods to treat or prevent ASD in a patient. The method includes the step of administering to a patient in need of treatment an effective amount of one of the carbamate compounds disclosed herein optionally in combination with an effective amount of one or more other compounds or therapeutic agents that have the ability to provide advantageous combined effects such as the ability to augment the activating effects of the compounds of the disclosure.

The present disclosure includes the use of isolated enantiomers of Formula (l). In one embodiment, a pharmaceutical composition comprising the isolated S-enantiomer of Formula (l) is used to provide treatment to a subject. In another embodiment, a pharmaceutical composition comprising the isolated R-enantiomer of Formula (1) is used to provide treatment to a subject.

The present disclosure also includes the use of mixtures of enantiomers of Formula (1). In one aspect, one enantiomer will predominate. An enantiomer that predominates in the mixture is one that is present in the mixture in an amount greater than any of the other enantiomers present in the mixture, e.g., in an amount greater than 50%. In one aspect, one enantiomer will predominate to the extent of 90% or to the extent of 91%, 92%, 93%, 94%, 95%, 96%, 97% or 98% or greater. In one particular embodiment, the enantiomer that predominates in a composition comprising a compound of Formula (1) is the S-enantiomer of Formula (1).

The present disclosure provides methods of using enantiomers and/or enantiomeric mixtures of compounds represented by Formula (1). A carbamate enantiomer of Formula (1) contains an asymmetric chiral carbon at the benzylic position, which is the second aliphatic carbon adjacent to the phenyl ring.

An isolated enantiomer is one that is substantially free of the corresponding enantiomer. Thus, an isolated enantiomer refers to a compound that is separated via separation techniques or prepared free of the corresponding enantiomer.

The term "substantially free," as used herein, means that the compound is made up of a significantly greater proportion of one enantiomer. In some embodiments, the compound includes at least about 90% by weight of a preferred enantiomer. In other embodiments, the compound includes at least about 99% by weight of a preferred enantiomer. Preferred enantiomers can be isolated from racemic mixtures by any method known to those skilled in the art, including high performance liquid chromatography (HPLC) and the formation and crystallization of chiral salts, or preferred enantiomers can be prepared by methods described herein.

Carbamate Compounds as Pharmaceuticals:

The present disclosure provides racemic mixtures, enantiomeric mixtures, and/or isolated enantiomers of Formula (1) as pharmaceuticals. The carbamate compounds are formulated as pharmaceuticals to provide treatment for ASD in a subject.

In general, the carbamate compounds of the present disclosure can be administered as pharmaceutical compositions by any method known in the art for administering therapeutic drugs including oral, buccal, topical, systemic (e.g., transdermal, intranasal, or by suppository), or parenteral (e.g., intramuscular, subcutaneous, or intravenous injection). Administration of the compounds directly to the nervous system can include, for example, administration to intracerebral, intraventricular, intracerebealventricar, intrathecal, intracisternal, intraspinal or peri-spinal routes of administration by delivery via intracranial or intravertebral needles or catheters with or without pump devices.

Compositions can take the form of tablets, pills, capsules, semisolids, powders, sustained release formulations, solutions, suspensions, emulsions, syrups, elixirs, aerosols, or any other appropriate compositions; and comprise at least one compound of this disclosure in combination with at least one pharmaceutically acceptable excipient. Suitable excipients are well known in the art, and they, and the methods of formulating the compositions, can be found in standard references such as Alfonso AR: *Remington's Pharmaceutical Sciences,* 17th ed., Mack Publishing Company, Easton PA, 1985, the disclosure of which is incorporated herein by reference in its entirety and for all purposes. Suitable liquid carriers, especially for injectable solutions, include water, aqueous saline solution, aqueous dextrose solution, and glycols.

In an embodiment, the carbamate compound is provided as an aqueous suspension. Aqueous suspensions of the disclosure can contain a carbamate compound in admixture with excipients suitable for the manufacture of aqueous suspensions. Such excipients can include, for example, a suspending agent, such as sodium carboxymethylcellulose, methylcellulose, hydroxypropylmethylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethylene oxycetanol), a condensation product of ethylene oxide with a partial ester derived from a fatty acid and a hexitol (e.g., polyoxyethylene sorbitol mono-oleate), or a condensation product of ethylene oxide with a partial ester derived from fatty acid and a hexitol anhydride (e.g., polyoxyethylene sorbitan mono-oleate).

The aqueous suspension can also contain one or more preservatives such as ethyl or n-propyl p-hydroxybenzoate, one or more coloring agents, one or more flavoring agents, and one or more sweetening agents, such as sucrose, aspartame or saccharin. Formulations can be adjusted for osmolarity.

Oil suspensions for use in the present methods can be formulated by suspending a carbamate compound in a vegetable oil, such as arachis oil, olive oil, sesame oil or coconut oil, or in a mineral oil such as liquid paraffin; or a mixture of these. The oil suspensions can contain a thickening agent, such as beeswax, hard paraffin or cetyl alcohol. Sweetening agents can be added to provide a palatable oral preparation, such as glycerol, sorbitol or sucrose. These formulations can be preserved by the addition of an antioxidant such as ascorbic acid. As an example of an injectable oil vehicle, see Minto, J. Pharmacol. Exp. Ther. 281:93-102, 1997. The pharmaceutical formulations of the disclosure can also be in the form of oil-in-water emulsions. The oily phase can be a vegetable oil or a mineral oil, described above, or a mixture of these.

Suitable emulsifying agents include naturally occurring gums, such as gum acacia and gum tragacanth, naturally occurring phosphatides, such as soybean lecithin, esters or partial esters derived from fatty acids and hexitol anhydrides, such as sorbitan mono-oleate, and condensation products of these partial esters with ethylene oxide, such as polyoxyethylene sorbitan mono-oleate. The emulsion can also contain sweetening agents and flavoring agents, as in the formulation of syrups and elixirs. Such formulations can also contain a demulcent, a preservative, or a coloring agent.

The compound of choice, alone or in combination with other suitable components can be made into aerosol formulations (i.e., they can be "nebulized") to be administered via inhalation. Aerosol formulations can be placed into pressurized acceptable propellants, such as dichlorodifluoromethane, propane, nitrogen, and the like.

Formulations of the present disclosure suitable for parenteral administration, such as, for example, by intraarticular (in the joints), intravenous, intramuscular, intradermal, intraperitoneal, and subcutaneous routes, can include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. Among the acceptable vehicles and solvents that can be employed are water and Ringer's solution, an isotonic sodium chloride. In addition, sterile fixed oils can conventionally be employed as a solvent or suspending medium. For this purpose, any bland fixed oil can be employed including synthetic mono- or diglycerides. In addition, fatty acids such as oleic acid can likewise be used in the preparation of injectables. These solutions are sterile and generally free of undesirable matter.

Where the compounds are sufficiently soluble they can be dissolved directly in normal saline with or without the use of suitable organic solvents, such as propylene glycol or polyethylene glycol. Dispersions of the finely divided compounds can be made-up in aqueous starch or sodium carboxymethyl cellulose solution, or in suitable oil, such as arachis oil. These formulations can be sterilized by conventional, wellknown sterilization techniques. The formulations can contain pharmaceutically acceptable auxiliary substances as required to approximate physiological conditions such as pH adjusting and buffering agents, toxicity adjusting agents, e.g., sodium acetate, sodium chloride, potassium chloride, calcium chloride, sodium lactate and the like.

The concentration of a carbamate compound in these formulations can vary widely, and will be selected primarily based on fluid volumes, viscosities, body weight, and the like, in accordance with the particular mode of administration selected and the patient's needs. For IV administration, the formulation can be a sterile injectable preparation, such as a sterile injectable aqueous or oleaginous suspension. This suspension can be formulated according to the known art using those suitable dispersing or wetting agents and suspending agents. The sterile injectable preparation can also be a sterile injectable solution or suspension in a nontoxic parenterally acceptable diluents or solvent, such as a solution of 1,3-butanediol. The formulations of commends can be presented in unitdose or multi-dose sealed containers, such as ampoules and vials. Injection solutions and suspensions can be prepared from sterile powders, granules, and tablets of the kind previously described.

In a particular embodiment, a carbamate compound is administered orally. The amount of the carbamate compound in the composition can vary widely depending on the type of composition, size of a unit dosage, kind of excipients, and other factors well known to those of ordinary skill in the art. In general, the final composition can comprise, for example, from 0.000001 percent by weight (% w) to 50% w of the carbamate compound, preferably 0.00001% w to 25% w, with the remainder being the excipient or excipients.

Pharmaceutical formulations for oral administration can be formulated using pharmaceutically acceptable carriers well known in the art in dosages suitable for oral administration. Such carriers enable the pharmaceutical formulations to be formulated in unit dosage forms as tablets, pills, powder, dragees, capsules, liquids, lozenges, gels, syrups, slurries, suspensions, etc. suitable for ingestion by the patient.

Formulations suitable for oral administration can consist of (a) liquid solutions, such as an effective amount of the pharmaceutical formulation suspended in a diluents, such as water, saline or PEG 400; (b) capsules, sachets or tablets, each containing a predetermined amount of the active ingredient, as liquids, solids, granules or gelatin; (c) suspensions in an appropriate liquid; and (d) suitable emulsions.

Pharmaceutical preparations for oral use can be obtained through combination of the compounds of the present disclosure with a solid excipient, optionally grinding a resulting mixture, and processing the mixture of granules, after adding suitable additional compounds, if desired, to obtain tablets or dragee cores. Suitable solid excipients are carbohydrate or protein fillers and include, but are not limited to sugars, including lactose, sucrose, mannitol, or sorbitol; starch from corn, wheat, rice, potato, or other plants; cellulose such as methyl cellulose, hydroxymethyl cellulose, hydroxypropylmethyl-cellulose or sodium carboxymethylcellulose; and gums including arabic and tragacanth; as well as proteins such as gelatin and collagen.

If desired, disintegrating or solubilizing agents can be added, such as the cross-linked polyvinyl pyrrolidone, agar, alginic acid, or a salt thereof, such as sodium alginate. Tablet forms can include one or more of lactose, sucrose, mannitol, sorbitol, calcium phosphates, corn starch, potato starch, microcrystalline cellulose, gelatin, colloidal silicon dioxide, talc, magnesium stearate, stearic acid, and other excipients, colorants, fillers, binders, diluents, buffering agents, moistening agents, preservatives, flavoring agents, dyes, disintegrating agents, and pharmaceutically compatible carriers. Lozenge forms can comprise the active ingredient in a flavor, e.g., sucrose, as well as pastilles comprising the active ingredient in an inert base, such as gelatin and glycerin or sucrose and acacia emulsions, gels, and the like containing, in addition to the active ingredient, carriers known in the art.

In an embodiment, the compound of the present disclosure is administered in the form of suppositories for rectal administration of the drug. These formulations can be prepared by mixing the drug with a suitable non-irritating excipient that is solid at ordinary temperatures but liquid at the rectal temperatures and will therefore melt in the rectum to release the drug. Such materials are cocoa butter and polyethylene glycols.

In an embodiment, the compound of the present disclosure is administered by intranasal, intraocular, intravaginal, and/or intrarectal routes including suppositories, insufflation, powders and aerosol formulations (for examples of steroid inhalants, see Rohatagi, J. Clin. Pharmacol. 35:1187-1193, 1995; Tjwa, Ann. Allergy Asthma Immunol. 75:107-111, 1995).

In an embodiment, the compound of the present disclosure is delivered transdermally, by a topical route, formulated as applicator sticks, solutions, suspensions, emulsions, gels, creams, ointments, pastes, jellies, paints, powders, and aerosols.

Encapsulating materials can also be employed with the compounds of the present disclosure and the term "composition" can include the active ingredient in combination with an encapsulating material as a formulation, with or without other carriers. For example, the compounds of the present disclosure can also be delivered as microspheres for slow release in the body. In one embodiment, microspheres can be administered via intradermal injection of drug (e.g., mifepristone)-containing microspheres, which slowly release subcutaneously (see Rao, J. Biomater Sci. Polym. Ed. 7:623-645, 1995; as biodegradable and injectable gel formulations (see, e.g., Gao, Pharm. Res. 12:857-863, 1995); or, as microspheres for oral administration (see, e.g., Eyles, J. Pharm. Pharmacol. 49:669-674, 1997). Both transdermal and intradermal routes afford constant delivery for weeks or months. Cachets can also be used in the delivery of the compounds of the present disclosure.

In another embodiment, the compound of the present disclosure is delivered by the use of liposomes which fuse with the cellular membrane or are endocytosed, i.e., by employing ligands attached to the liposome that bind to surface membrane protein receptors of the cell resulting in endocytosis. The active drug can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

By using liposomes, particularly where the liposome surface carries ligands specific for target cells, or are otherwise preferentially directed to a specific organ, one can focus the delivery of the carbamate compound into target cells in vivo (See, e.g., AlMuhammed, J. Microencapsul. 13:293-306, 1996; Chonn, Curr. Opin. Biotechnol. 6:698-708, 1995; Ostro, Am. J. Hosp. Pharm. 46:1576-1587, 1989).

In various embodiment, the compound of the present disclosure is provided as a salt and can be formed with many acids, including but not limited to hydrochloric, sulfuric, acetic, lactic, tartaric, malic, succinic, etc. Salts tend to be more soluble in aqueous or other protonic solvents that are the corresponding free base forms. In other cases, the preferred preparation can be a lyophilized powder which can contain, for example, any or all of the following: 1 mM-50 mM histidine, 0.1%-2% sucrose, 2%-7% mannitol, at a pH range of 4.5 to 5.5 that is combined with buffer prior to use.

Pharmaceutically acceptable salts and esters refers to salts and esters that are pharmaceutically acceptable and have the desired pharmacological properties. Such salts include salts that may be formed where acidic protons present in the compounds are capable of reacting with inorganic or organic bases. Suitable inorganic salts include those formed with the alkali metals, e.g. sodium and potassium, magnesium, calcium, and aluminum. Suitable organic salts include those formed with organic bases such as the amine bases, e.g. ethanolamine, diethanolamine, triethanolamine, tromethamine, N methylglucamine, and the like. Pharmaceutically acceptable salts can also include acid addition salts formed from the reaction of amine moieties in the parent compound with inorganic acids (e.g. hydrochloric and hydrobromic acids) and organic acids (e.g. acetic acid, citric acid, maleic acid, and the alkane- and arene-sulfonic acids such as methanesulfonic acid and benzenesulfonic acid). Pharmaceutically acceptable esters include esters formed from carboxy, sulfonyloxy, and phosphonoxy groups present in the compounds. When there are two acidic groups present, a pharmaceutically acceptable salt or ester may be a monoacid-mono-salt or ester or a di-salt or ester; and similarly where there are more than two acidic groups present, some or all of such groups can be salified or esterified.

Compounds described in this disclosure can be present in unsalified or unesterified form, or in salified and/or esterified form, and the naming of such compounds is intended to include both the original (unsalified and unesterified) compound and its pharmaceutically acceptable salts and esters. The present disclosure includes pharmaceutically acceptable salt and ester forms of Formula (l). More than one crystal form of an enantiomer of Formula (l) can exist and as such are also included in the present disclosure.

A pharmaceutical composition of the disclosure can optionally contain, in addition to a carbamate compound, at least one other therapeutic agent useful in the treatment of ASD. For example, the carbamate compounds of Formula (l) can be combined physically with other activating or stimulant compound(s) in fixed dose combinations to simplify their administration.

Methods of formulating pharmaceutical compositions have been described in numerous publications such as *Pharmaceutical Dosage Forms: Tablets*. Second Edition. Revised and Expanded. Volumes 1-3, edited by Lieberman et al; *Pharmaceutical Dosage Forms*: Parenteral Medications. Volumes 1-2, edited by Avis et al; and *Pharmaceutical Dosage Forms: Disperse Systems*. Volumes 1-2, edited by Lieberman et al; published by Marcel Dekker, Inc., the disclosure of which are herein incorporated by reference in their entireties and for all purposes.

The pharmaceutical compositions are generally formulated as sterile, substantially isotonic and in full compliance with all Good Manufacturing Practice (GMP) regulations of the U.S. Food and Drug Administration.

Dosage Regimens

The present disclosure provides methods of treating ASD in a mammal using carbamate compounds. The amount of the carbamate compounds necessary to provide treatment for ASD is defined as a therapeutically or a pharmaceutically effective dose. The dosage schedule and amounts effective for this use, i.e., the dosing or dosage regimen will depend on a variety of factors including the stage of the disease, the patient's physical status, age and the like. In calculating the dosage regimen for a patient, the mode of administration is also taken into account.

A person of ordinary skill in the art will be able without undue experimentation, having regard to that skill and this disclosure, to determine a therapeutically effective amount of a particular substituted carbamate compound for practice of this invention (see, e.g., Lieberman, Pharmaceutical Dosage Forms (Vols. 1-3, 1992); Lloyd, 1999, The art, Science and Technology of Pharmaceutical Compounding; and Pickar, 1999, Dosage Calculations). A therapeutically effective dose is also one in which any toxic or detrimental side effects of the active agent is outweighed in clinical terms by therapeutically beneficial effects. It is to be further noted that for each particular subject, specific dosage regimens should be evaluated and adjusted over time according to the individual need and professional judgment of the person administering or supervising the administration of the compounds.

For treatment purposes, the compositions or compounds disclosed herein can be administered to the subject in a single bolus delivery, via continuous delivery over an extended time period, or in a repeated administration protocol (e.g., by an hourly, daily or weekly, repeated administration protocol). The pharmaceutical formulations can be administered, for example, one or more times daily, 3 times per week, or weekly. In one embodiment, the pharmaceutical formulations are orally administered once or twice daily.

In this context, a therapeutically effective dosage of the biologically active agent(s) can include repeated doses within a prolonged treatment regimen that will yield clinically significant results to provide treatment for ASD. Determination of effective dosages in this context is typically based on animal model studies followed up by human clinical trials and is guided by determining effective dosages and administration protocols that significantly reduce the occurrence or severity of targeted exposure symptoms or conditions in the subject. Suitable models include, for example, murine, rat, porcine, feline, non-human primate, and other accepted animal model subjects known in the art. Alternatively, effective dosages can be determined using in vitro models (e.g., immunologic and histopathologic assays).

Using such models, only ordinary calculations and adjustments are typically required to determine an appropriate concentration and dose to administer a therapeutically effective amount of the biologically active agent(s) (e.g., amounts that are intranasally effective, transdermally effective, intravenously effective, or intramuscularly effective to elicit a desired response).

In an exemplary embodiment, unit dosage forms of the compounds are prepared for standard administration regimens. In this way, the composition can be subdivided readily into smaller doses at the physician's direction. For example, unit dosages can be made up in packeted powders, vials or ampoules and preferably in capsule or tablet form.

The active compound present in these unit dosage forms of the composition can be present in an amount of, for example, from about 10 mg to about one gram or more, for single or multiple daily administration, according to the particular need of the patient. By initiating the treatment regimen with a minimal daily dose of about one gram, the blood levels of the carbamate compounds can be used to determine whether a larger or smaller dose is indicated.

In an exemplary embodiment, the therapeutically effective amount of the compound of Formula (I) is from about 0.01 mg/kg/dose to about 300 mg/kg/dose. Effective administration of the carbamate compounds can be, for example, at an oral or parenteral dose of from about 0.01 mg/kg/dose to about 150 mg/kg/dose. For example, administration can be from about 0.1 mg/kg/dose to about 25 mg/kg/dose, e.g., from about 0.2 to about 18 mg/kg/dose, e.g., from about 0.5 to about 10 mg/kg/dose. Therefore, the therapeutically effective amount of the active ingredient can be, for example, from about 1 mg/day to about 7000 mg/day for a subject having, for example, an average weight of 70 kg, e.g., from about 10 to about 2000 mg/day, e.g., from about 50 to about 600 mg/day, e.g., about 10, 25, 50, 75, 100, 125, 150, 175, 200, 225, 250, 275, 300, 325, 350, 375, 400, 425, 450, 475, 500, 525, 550, 575, or 600 mg/day or more or any range therein. In one embodiment, the compound of Formula (l) is administered in the form of a capsule at a dose of about 150 mg to about 300 mg without any excipients.

In an embodiment, this disclosure also provides kits for use in providing treatment for ASD. After a pharmaceutical composition comprising one or more carbamate compounds, with the optional addition of one or more other compounds of therapeutic benefit, has been formulated in a suitable carrier, it can be placed in an appropriate container and labeled for providing treatment for ASD. Additionally, another pharmaceutical comprising at least one other therapeutic agent can be placed in the container as well and labeled for treatment of the indicated disease. Such labeling can include, for example, instructions concerning the amount, frequency and method of administration of each pharmaceutical.

Although the foregoing invention has been described in detail by way of example for purposes of clarity of understanding, it will be apparent to the artisan that certain changes and modifications are comprehended by the disclosure and may be practiced without undue experimentation within the scope of the appended claims, which are presented by way of illustration not limitation. The following examples are provided to illustrate specific aspects of the invention and are not meant to be limitations.

Example

Preparation of Test Compound

This study was undertaken to determine the effect of the (D) or (R) enantiomer of a phenylalkylamino carbamate of Formula (l), specifically Ocarbamoyl-(D)-phenylalaninol which can also be named (R)-(beta-amino-benzenepropyl) carbamate shown above as Formula (lb), referred to herein as "Test compound". The Test compound was prepared by the synthesis methods of Examples I to III disclosed in WO1996/07637.

In Vivo Model

Therapeutic effects of the Test compound were examined in a series of experiments in vivo to determine the effect on structural and behavioral abnormalities in MeCP2-deficient animals. The in vivo model is known to be predictive of ASD. Impairments in cortical sensory processing have been demonstrated in Rett syndrome (RTT) and Autism Spectrum Disorders (ASD) and are thought to contribute to highorder phenotypic deficits. MeCP2+/−model may be useful for preclinical development targeting specific cortical processing abnormalities in RTT with potential relevance to ASD. (Neurobiol Dis. 2012 April; 46(1):88-92.). MeCP2 immunofluorescence in autism and other neurodevelopmental disorders was quantified by laser scanning cytometry and compared with control postmortem cerebral cortex samples on a large tissue microarray. A significant reduction in MeCP2 expression compared to age-matched controls was found in 11/14 autism (79%), 9/9 RTT (100%), 4/4 Angelman syndrome (100%), 3/4 Prader-Willi syndrome (75%), 3/5 Down syndrome (60%) frontal cortex samples. (Epigenetics. 2006; 1(4): el-11.)

Studies employed wild type (WT) mice and heterozygous MeCP2 knockout mice (HET). All mice were provided by Jackson Laboratory, Bar Harbor, Me. HET mice were Bird mice (Jackson Laboratories, Bar Harbor, Me., B6.129P2(C)-Mecp2.sup.tm1.1Bird/Stock Number: 003890) were obtained by crossing knockout females (HET) with wild type (WT) males (C57B/6J). 129P2(C)-Mecp2.sup.tml.1Bird/J is a constitutive Mecp2 knockout that exhibits Rett syndrome-like neurological defects.

Breeding of the test mice done at SK Biopharmaceuticals, MeCP2 knockout mice (Null and HET) were used for neuronal morphological assay and motor behavioral test, respectively. The recent studies identified genetic mutations of the MeCP2 gene in autism patients, which were previously considered to be associated primarily with RTT, and another results suggest that both genetic and epigenetic defects lead to reduced MeCP2 expression and may be important in the complex etiology of autism. (Molecular Autism volume 8, Article number: 43 (2017), Epigenetics. 2006; 1(4): el-11.)

Experimental Example 1: Morphological Recovery of MeCP2 KO Primary Neuron (1) Method MeCP2 KO mouse primary cortical neurons were cultured at PO and morphological change was analyzed via immunocytochemistry.

BDNF (50 ng/ml) or Test compound (80 and 2000 nM) was treated from DIV1 to indicated days. At DIV5, the neurite outgrowth was analyzed with MAP2 immunostaining for analysis of neurite formation.

MeCP2 KO mouse primary cortical neurons were cultured at PO and morphological change was analyzed via immunocytochemistry.

BDNF (50 ng/ml) or Test compound (1000 nM) was treated from DIV1 to indicated days. At DIV14, synaptogenesis and soma size were analyzed with Synapsin-1, MAP2 immunostaining and nuclear staining with Hoechst.

(2) Result

The loss of MeCP2 leads to the inability of synapse and the neurite formation and reduction of soma size compromised to mature in brain. These are RTT specific neuronal phenotypes in both MeCP2 animal and RTT patients. Test compound significantly enhanced the neurite length to a level similar to that of BDNF and significantly enhanced synaptogenesis and soma size (FIGS. 1 to 3).

Experimental Example 2: Survival Rate (1) Method

Test groups are as below

Vehicle Null group: vehicle (0.9% saline, 10 ml/kg)

Test compound Null group: 100 mg/kg, po in 0.9% saline

About 5 week old Null mice were treated with daily oral injections of the vehicle or Test compound. MeCP2 knock-out mice (Null) survival rate test was conducted until all animals were dead.

(2) Result

Compared to vehicle-treated Null mice, Null mice treated with Test compound (100 mg/kg) showed 42.7% increase of ILS %. And significant enhancement of life span. ($P<0.0046$, Log lank test)

ILS (Independent living scale)%: 100×(median survival days of test group-median survival days of vehicle group)/median survival days of vehicle group (FIG. 4).

Experimental Example 3: Body Weight (1) Method

Test groups are as below

Vehicle WT group: vehicle (0.9% saline, 10 ml/kg)

Vehicle HET group: vehicle (0.9% saline, 10 ml/kg)

Test compound HET group: 100 mg/kg, po in 0.9% saline

About 5 week old WT and HET mice were treated with daily oral injections of the vehicle or Test compound. Treatment conducted until the mice became 16 weeks old.

(2) Result

No differences were observed in body weight between vehicle-treated wild-type and HET control mice. Test compound did not affect the body weight change of HET animals for chronic treatment (FIG. 5).

Experimental Example 4: Accelerating Rotarod Test and Clasping (1) Method

The rotarod test is widely used to evaluate the motor coordination of rodents, and is especially sensitive in detecting cerebellar dysfunction. The motor performance on the rotarod can be influenced by several factors, such as motor coordination, learning and cardiopulmonary endurance. Since several studies have shown that basal ganglia are essential in motor skill learning of serial motor sequence. The test measures parameters such as riding time (seconds) or endurance (RPM).

Mice were placed on the rotarod apparatus (Ugo basile, Italy) consisting of a rod that rotates at a constant or variable and accelerating speed of 4 rpm. Once a mouse loses its balance and falls onto an underlying platform, the timer automatically stops. Mice were exposed to the apparatus for 5 min training at a constant speed (4 rpm) and placed back on the rod after each fell. After a rest period of at least 1 hr, animals were placed back on the rotarod apparatus for testing. Once all animals in a test session were loaded on the rod, the rotarod apparatus was placed on accelerating speed (0-40 rpm) over 5 min and then the first falling time was recorded. The test was repeated three consecutive times per animal. For each test session, the RPM score at time of fall off the rod were recorded.

(2) Result

Vehicle-treated HET mice fell more rapidly and at lower speeds compared to vehicle-treated WT mice. Test compound-treated mice took more time to fall off from the rod and fell at higher speeds compared to vehicle-treated HET mice (FIG. 6).

Vehicle-treated HET mice clasped more than vehicle-treated wild type mice. Mice treated with Test compound (100 mg/kg) clasped less than vehicle-treated HET mice (FIG. 7).

CONCLUSION

Abnormal neurite formation, reduced soma size and dysregulation of synaptogenesis are key phenotypes in neuronal cells in both rodent and human cause dysregulations of MeCP2 gene. Test compound is effective in ameliorating neuronal phenotypes by dysregulations of MeCP2 gene via primary neuron potential improvements in synaptic function in brain. Test compound could lead to improved motor function and survival rate in MeCP2 KO female and male mice, respectively.

Therefore, the compound of Formula (I) including Test compound could improve neurologic deficits in Rett syndrome and other ASDs.

The invention claimed is:

1. A method of treating autism spectrum disorder (ASD) or one or more symptoms of ASD in a subject, comprising:

administering to a subject in need thereof a therapeutically effective amount of a compound of Formula (I):

(I)

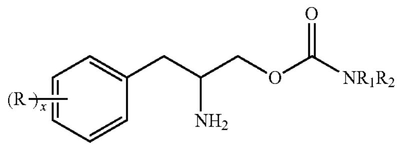

or a pharmaceutically acceptable salt or ester thereof;

wherein R is selected from the group consisting of —H, alkyl, halo, alkoxy, nitro, hydroxy, haloalkyl, and thioalkoxy;

x is an integer of 1 to 3, with the proviso that R may be the same or different when x is 2 or 3; and $R_1$ and $R_2$ are independently selected from the group consisting of —H, alkyl, aryl, arylalkyl, and cycloalkyl; or $R_1$ and $R_2$ together form a 5 to 7-membered heterocyclic group which is optionally substituted with alkyl or aryl, wherein the heterocyclic group can comprise 1 to 2 nitrogen atoms and 0 to 1; oxygen atom, wherein the nitrogen atoms are not directly connected with each other or with the oxygen atom.

2. The method of claim 1, wherein R is a member selected from the group consisting of —H, lower alkyl of 1 to 8 carbon atoms, halo selected from F, CI, Br and I, alkoxy containing 1 to 3 carbon atoms, nitro, hydroxy, trifluoromethyl, and thioalkoxy containing 1 to 3 carbon atoms;

x is an integer of 1 to 3, with the proviso that R may be the same or different when x is 2 or 3;

$R_1$ and $R_2$ can be the same or different from each other and are independently selected from the group consisting of —H, lower alkyl of 1 to 8 carbon atoms, aryl, arylalkyl, cycloalkyl of 3 to 7 carbon atoms; or $R_1$ and $R_2$ can be joined to form a 5 to 7-membered heterocycle substituted with a member selected from the group consisting of —H, alkyl, and aryl groups, wherein the cyclic compound can comprise 1 to 2 nitrogen atoms and 0 to 1 oxygen atom, wherein the nitrogen atoms are not directly connected with each other or with the oxygen atom.

3. The method of claim 1 wherein R is —H and x is 1.

4. The method of claim 1 wherein each of R, $R_1$ and $R_2$ is —H and x is 1.

5. The method of claim 1, wherein the compound of Formula (I) is an enantiomer of Formula (I) substantially free of other enantiomers or an enantiomeric mixture wherein one enantiomer of Formula (I) predominates.

6. The method of claim 5, wherein the enantiomer of Formula (I) predominates to the extent of about 90% or greater.

7. The method of claim 5, wherein the enantiomer of Formula (I) predominates to the extent of about 98% or greater.

8. The method of claim 5, wherein the enantiomer of Formula (I) is an enantiomer of Formula (Ia):

(Ia)

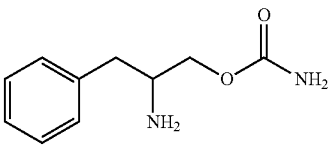

or a pharmaceutically acceptable salt or ester thereof.

9. The method of claim 8, wherein the enantiomer of Formula (Ia) is (R) or (D) enantiomer.

10. The method of claim 8, wherein the enantiomer of Formula (Ia) is the(S) or (L) enantiomer.

11. The method of claim 8, wherein the enantiomer of Formula (Ia) predominates to the extent of about 90% or greater.

12. The method of claim 8, wherein the enantiomer of Formula (Ia) predominates to the extent of about 98% or greater.

13. The method of claim 5, wherein the enantiomer of Formula (I) substantially free of other enantiomers is the compound of Formula (lb) or an enantiomeric mixture wherein the compound of Formula (lb) predominates:

(Ib)

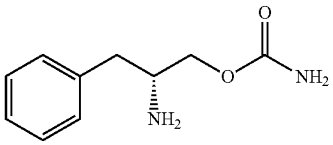

or a pharmaceutically acceptable salt or ester thereof.

14. The method of claim 13, wherein the compound of Formula (lb) predominates to the extent of about 90% or greater.

15. The method of claim 13, wherein the compound of Formula (lb) predominates to the extent of about 98% or greater.

16. The method of claim 1, wherein the autism spectrum disorder (ASD) is chosen from the group consisting of autism, autistic disorder, Asperger syndrome, Rett syndrome, Angelman syndrome, Williams syndrome, Pervasive Developmental Disorder Not Otherwise Specified (PDD-NOS), Childhood Disintegrative Disorder, and Smith-Magenis Syndrome.

17. The method of claim 16, wherein the autism spectrum disorder (ASD) is Rett syndrome.

18. The method of claim 16, wherein the autism spectrum disorder (ASD) is autism.

19. The method of claim 1, wherein the treatment reduces one or more symptoms selected from the group consisting of anxiety, impairment in social interaction, impairment in the use of multiple nonverbal behaviors, failure to develop peer relationships appropriate to developmental level, lack of spontaneous seeking to share enjoyment, interests, or achievements, lack of social or emotional reciprocity, impairment in communication, restricted and repetitive interests and behaviors, lack of spontaneous make-believe play, abnormal fear conditioning, abnormal social behavior, repetitive behavior, abnormal nocturnal behaviour, seizure activity, abnormal locomotion, abnormal expression of Phospho-ERK1/2, abnormal expression of Phospho-Akt, and bradycardia.

20. The method of claim 1, wherein the therapeutically effective amount of the compound of Formula (I) is from about 0.01 mg/kg/dose to about 300 mg/kg/dose.

* * * * *